United States Patent [19]

Howell

[11] 4,125,724

[45] Nov. 14, 1978

[54] HYDROGENATION PROCESS

[75] Inventor: Henry G. Howell, East Syracuse, N.Y.

[73] Assignee: Bristol-Myers Company, New York, N.Y.

[21] Appl. No.: 839,947

[22] Filed: Oct. 6, 1977

Related U.S. Application Data

[63] Continuation-in-part of Ser. No. 645,001, Dec. 29, 1975, abandoned.

[51] Int. Cl.$^2$ ............................................. C07D 241/20
[52] U.S. Cl. ..................................... 544/336; 544/102; 260/347.3; 260/347.4; 544/168; 260/404; 260/551 R; 544/224; 260/557 R; 260/561 R; 544/235; 260/346.73; 260/562 R; 544/237; 260/562 A; 260/562 P; 544/249; 544/258; 544/277; 544/292; 544/332; 544/356; 548/337; 548/372; 546/309; 546/138; 546/143; 546/159; 546/122; 546/108; 546/105; 546/88; 546/87; 260/307 R; 260/307 G; 260/308 R; 260/308 A; 260/308 D; 260/326.14 R; 260/326.13 B; 260/326.2; 260/345.2; 260/345.7 R

[58] Field of Search ........ 260/250 BN, 562 R, 561 R, 260/557 R, 295 AM, 347.3, 345.7, 326.13 B, 562 P, 562 A, 347.4; 544/336

[56] References Cited

PUBLICATIONS

Sebatier et al., Compt. Rend. 144, 824–826, (1907).
Brown et al., J. Am. Chem. Society 88, 1464, (1966).
Viola et al., Chem. Ber. 101, 3517, (1968).
Lorenz et al., J. Org. Chem. 28, 1707, (1963).
Ojima et al., Tetrahedron Letters No. 44, 4363–4366 (1973).

Primary Examiner—Jose Tovar
Attorney, Agent, or Firm—David M. Morse

[57] ABSTRACT

An improved and novel process is provided for the reduction of isocyanate groups in organic compounds to formamide groups by catalytic hydrogenation with a noble metal catalyst. The process allows preparation of formamides in consistently high yields from all types of isocyanates.

3 Claims, No Drawings

HYDROGENATION PROCESS

CROSS-REFERENCE TO RELATED APPLICATION

This application is a continuation-in-part application of co-pending application Ser. No. 645,001 filed Dec. 29, 1975, now abandoned.

This invention relates to a new and improved process for the reduction of isocyanate groups in organic compounds to formamide groups. More particularly, the process of the present invention comprises hydrogenating a monoisocyanate organic compound of the general formula R—N=C=O wherein R represents $C_1$-$C_{20}$ alkyl, $C_3$-$C_{12}$ cycloalkyl, aryl (e.g. phenyl or naphthyl) or a heterocyclic group which contains one or more ring hetero atoms selected from oxygen and nitrogen in addition to at least one ring carbon atom and which is linked to the nitrogen atom of the isocyanate moiety through a ring carbon atom, said R group being optionally substituted by $C_1$-$C_6$ alkyl, $C_1$-$C_6$ alkoxy, phenyloxy, naphthyloxy, halo, trifluoromethyl, $C_1$-$C_6$ alkanoyloxy, $C_1$-$C_6$ alkanoylamino, carb($C_1$-$C_6$ alkoxy)carbonyl-$C_1$-$C_6$-alkyl or phenyl, with a noble metal catalyst in an inert aprotic organic solvent in the presence of a catalytic amount of a tertiary amine for a time sufficient to produce the corresponding formamide compound of the formula R—NH—CHO.

Preparation of a wide variety of isocyanate compounds has been recently facilitated by the Weinstock modification of the Curtius rearrangement [J. Org. Chem. 26:3511 (1961)] and by other methods such as those disclosed by Washburne, et al. in Syn. Comm. 2:227 (1972) and by Yamada, et al. in J. Amer. Chem. Soc. 94:6203 (1972). These isocyanates may be used to prepare the corresponding formamides which are stable versatile compounds useful, for example, as precursors of primary, secondary and tertiary amines.

Various problems have been encountered in the known methods of obtaining formamides from isocyanates.

Metal hydrides such as lithium aluminum hydride and aluminum hydride have been found to reduce isocyanates to N-methylamines and not formamides [see, for example, J. Amer. Chem. Soc. 88:1464 (1966); Monatsh. 82:621 (1951) and Chem. Ber. 101:3517 (1968)]. While the N-methylamines can be converted to amines, much more vigorous reaction conditions are required for removal of the N-methyl group than for the formyl group.

The reduction of isocyanates to formamides using triphenyltin hydride has been reported by Lorenz and Becker in J. Org. Chem. 28:1707 (1963). This method, however, gives yields in the range of only about 40–55% and appears to be restricted to the more reactive isocyanates.

A two-step process involving the hydrosilation of isocyanates catalyzed by palladium is disclosed by Ojima, et al. in Tetrahedron Letters:4363 (1973). The silylformamides obtained in the hydrosilation step are solvolyzed with methanol to the desired formamides. Yields in this process are again highly variable depending on the nature of the isocyanate starting material. Thus, with aryl isocyanates such as phenyl isocyanate, yields are reported as being nearly quantitative, but alkyl formamides such as n-butyl formamide are obtained in less than 50% yield.

While attempts have been made to reduce isocyanates by hydrogenation, the results have been unsatisfactory and formamides have not been produced. Sebatier and Mailke are reported in Compt. rend. 144:824–826 (1907) to have reduced ethyl isocyanate and phenyl isocyanate at 190° C. by conducting hydrogen gas and vaporized isocyanate over nickel. The products from ethyl isocyanate were a mixture of ethylamine, methylethylamine, diethylamine and triethylamine. Reduction of phenyl isocyanate gave a mixture of methane, aniline and diphenylurea.

The catalytic hydrogenation method of the present invention advantageously provides a general and simple process for selectively reducing isocyanate functional groups to formamide groups in consistently high yields. The method is found to give good results with alkyl and cycloalkyl isocyanates as well as the more reactive aryl and heterocyclic compounds and is mild enough to be used with isocyanate compounds containing functional groups which might be adversely affected by the more vigorous reaction conditions of the prior art procedures.

In performing the process of the present invention, the isocyanate starting material is dissolved in an inert aprotic solvent. Suitable aprotic solvents are those which will dissolve the isocyanate without reacting with it. Examples of such solvents include dioxane, benzene, tetrahydrofuran, diethyl ether, toluene, xylene, cyclohexane and diethylene glycol dimethyl ether. Since the isocyanates are readily decomposed by the presence of water, it is preferred to use anhydrous solvents.

The hydrogenation is accomplished by use of a noble metal hydrogenation catalyst. The preferred catalysts are those containing either platinum or palladium. Platinum may be used in the form of platinum black but is advantageously employed as the oxide ($PtO_2$) or on a conventional inert carrier material such as carbon, barium sulfate, calcium carbonate, diatomaceous earth, etc. Palladium like platinum may be used as palladium black or palladium oxide but is most preferably employed supported on a conventional inert carrier such as carbon, barium sulfate, barium carbonate or diatomaceous earth. The ratio of catalyst to starting material is not critical. A convenient amount of catalyst to use in the process has been found to be about 0.5 gram of catalyst per 100 ml. of isocyanate solution.

Temperatures and pressures for the hydrogenation are not critical. The pressure may be varied from around atomspheric pressure up to the practical limits of the hydrogenation apparatus used. Temperatures may be varied over a wide range and are limited only by the apparatus and the nature of the solvent (boiling point) and isocyanate starting material (decomposition point). Good results have been obtained at room temperature and a pressure of about 50 p.s.i. of hydrogen (approximately 3 atmospheres).

The hydrogenation is effected for the time necessary to obtain reduction of the particular isocyanate starting material to the corresponding formamide. Times are dependent on the nature of the starting material and can be determined by routine experimentation.

A catalytic amount of a tertiary amine is added to the isocyanate, solvent and noble metal catalyst before beginning the hydrogenation. Examples of suitable amines include pyridine, N-methylpiperidine, picoline, lutidine and trialkylamines such as trimethylamine and triethylamine. While the hydrogenation can be accomplished without the tertiary amine, addition of the amine catalyst is found to greatly accelerate the reaction, particularly for the less reactive alkyl and cycloalkyl isocyanates which would otherwise require impractically long reaction times.

The hydrogenation process of the present invention can be used to reduce isocyanate functional groups to formamide groups in any organic compound. While any known isocyanate will be converted to the corresponding formamide, an isocyanate starting material R—N═C═O having functional groups, other than the isocyanate moiety, reducible by catalytic hydrogenation, e.g. N-benzyl, O-benzyl and carbobenzoxy, will have these groups reduced along with isocyanate group during the course of the reaction. The mildness and specificity of the process, however, makes it applicable as a general class reaction for preparation of formamides from those isocyanates having functional groups compatible with hydrogenation conditions.

Examples of preferred isocyanate starting materials which can be used in the process include those in which R is alkyl, cycloalkyl, aryl or nitrogen- and/or oxygen-containing heterocyclic. The R group may be either unsubstituted or may be substituted with one or more substituents selected from $C_1$–$C_6$ alkyl, $C_1$–$C_6$ alkoxy, aryloxy (e.g. phenyloxy or naphthyloxy), halo (chloro, bromo, fluoro or iodo), trifluoromethyl, $C_1$–$C_6$ alkanoyloxy, $C_1$–$C_6$ alkanoylamino, carb($C_1$–$C_6$)- alkoxy (e.g. —$COOC_2H_5$), $C_1$–$C_6$ alkoxycarbonyl-$C_1$–$C_6$ alkyl (e.g. ethoxycarbonylmethyl) or phenyl. Protected amino and protected hydroxy substituents other than the groups mentioned above may also be used providing the protecting group is stable to hydrogenation, e.g. O-tetrahydropyranyl.

The term "alkyl" as used above includes both straight and branched chain saturated aliphatic hydrocarbon radicals having from 1 to 20, preferably from 1 to 12 and most preferably 1 to 6, carbon atoms such as methyl, ethyl, n-propyl, isopropyl, n-butyl, isobutyl, t-butyl, amyl, isoamyl and the isomeric hexyl radicals.

"Cycloalkyl" refers to saturated cycloaliphatic hydrocarbon radicals having from 3 to 12 and most preferably 3 to 7 carbon atoms, e.g. cyclopropyl, cyclobutyl, cyclopentyl, cyclohexyl and cycloheptyl.

"Aryl" includes mono- (e.g. phenyl), bi- (e.g. 1-naphthyl, 2-naphthyl) and poly-cyclic (e.g. 9-anthryl, 2-phenanthryl) aromatic hydrocarbon radicals and is most preferably phenyl or naphthyl.

"Heterocyclic" groups include monocyclic, bicyclic or polycyclic ring systems containing one or more (preferably 1 to 4) ring hetero atoms selected from oxygen and nitrogen in addition to at least one ring carbon atom, said heterocyclic ring being linked to the nitrogen atom of the isocyanate moiety through a ring carbon atom. As used herein the term heterocyclic includes radicals of aromatic character as well as appropriate partially or wholly saturated residues. It is preferred, however, that saturated nitrogen-containing heterocycles such as piperidyl, piperazinyl or morpholinyl have an alkyl ($C_1$–$C_6$) or aryl (e.g. phenyl or naphthyl) substituent on the nitrogen atom so as to minimize side reactions. Examples of suitable heterocyclic radicals include pyrrolyl (e.g. 3-pyrrolyl), 2H-pyrrolyl (e.g. 2H-pyrrol-3-yl), imidazolyl (e.g. 2-imidazolyl), pyridyl (e.g. 3-pyridyl), pyrazinyl, pyrimidinyl (e.g. 2-pyrimidinyl), pyridazinyl (e.g. 3-pyridazinyl), indolizinyl (e.g. 2-indolizinyl), 3H-indolyl (e.g. 3H-indol-2-yl), furyl (e.g. 3-furyl), pyranyl (e.g. 2H-pyran-3-yl), isobenzofuranyl (e.g. 1-isobenzofuranyl), chromenyl (e.g. 2H-chromen-3-yl), indolyl (e.g. 2-indolyl), indazolyl (e.g. 1H-indazol-3-yl), purinyl (e.g. 8-purinyl), 4H-quinolizinyl (e.g. 4H-quinolizin-2-yl), isoquinolyl (e.g. 3-isoquinolyl), quinolyl (e.g. 2-quinolyl), phthalazinyl (e.g. 1-phthalazinyl), naphthyridinyl (e.g. 1,8-naphthyridin-2-yl), quinoxalinyl (e.g. 2-quinoxalinyl), quinazolinyl (e.g. 2-quinazolinyl), cinnolinyl (e.g. 3-cinnolinyl), pteridinyl (e.g. 2-pteridinyl), $\beta$-carbolinyl (e.g. $\beta$-carbolin-3-yl), phenanthridinyl (e.g. 3-phenanthridinyl), acridinyl (e.g. 2-acridinyl), permidinyl (e.g. 2-permidinyl), phenanthrolinyl (e.g. 1,7-phenanthrolin-3-yl), isoxazolyl (e.g. 3-isoxazolyl), furazanyl (e.g. 3-furazanyl), phenoxazinyl (e.g. 2-phenoxazinyl), pyrrolidinyl (e.g. 2-pyrrolidinyl), pyrrolinyl (e.g. 2-pyrrolin-3-yl), imidazolidinyl (e.g. 2-imidazolidinyl), piperidyl (e.g. 2-piperidyl), morpholinyl (e.g. 3-morpholinyl), oxadiazolyl (e.g. 1,3,4-oxadiazol-5-yl), triazolyl (e.g. 1,2,3-triazol-5-yl, 1,3,4-triazol-5-yl), oxazolyl (e.g. 1,4-oxazol-5-yl), tetrazolyl (e.g. tetrazol-5-yl) and tetrahydrofuryl. The heterocyclic radical may be unsubstituted or substituted by one or more (preferably 1 or 2) of the substituent groups mentioned above.

Specific examples of preferred isocyanates which may be used as starting materials include monoisocyanates of the formula R—N═C═O where R is (1) $C_1$–$C_{20}$ alkyl: e.g. methyl isocyanate, ethyl isocyanate, n-propyl isocyanate, isopropyl isocyanate, n-butyl isocyanate, isobutyl isocyanate, sec-butyl isocyanate, t-butyl isocyanate n-hexyl isocyanate, octyl isocyanate, dodecyl isocyanate or octadecyl isocyanate;

(2) $C_3$–$C_7$ cycloalkyl optionally substituted with one or more (preferably one) substituents selected from $C_1$–$C_6$ alkyl, $C_1$–$C_6$ alkoxy, phenyloxy, naphthyloxy, halo, trifluoromethyl, $C_1$–$C_6$ alkanoyloxy, $C_1$–$C_6$ alkanoylamino, carb($C_1$–$C_6$)alkoxy, $C_1$–$C_6$ alkoxycarbonyl $C_1$–$C_6$ alkyl or phenyl; e.g. cyclopropyl isocyanate, 2-phenylcyclopropyl isocyanate, cyclobutyl isocyanate or cyclohexyl isocyanate;

(3) aryl selected from phenyl and naphthyl, said aryl radical being unsubstituted or substituted by one or more (preferably 1 or 2) $C_1$–$C_6$ alkyl, $C_1$–$C_6$ alkoxy, phenyloxy, naphthyloxy, halo, trifluoromethyl, $C_1$–$C_6$ alkanoyloxy, $C_1$–$C_6$ alkanoylamino, carb($C_1$–$C_6$)-alkoxy, $C_1$–$C_6$ alkoxycarbonyl-$C_1$–$C_6$ alkyl or phenyl; e.g. phenyl isocyanate, p-bromophenyl isocyanate, m-chlorophenyl isocyanate, o-chlorophenyl isocyanate, p-chlorophenyl isocyanate, 2,5-dichlorophenyl isocyanate, m-methoxyphenyl isocyanate, o-methoxyphenyl isocyanate, 1-naphthyl isocyanate, 2-naphthyl isocyanate, m-tolyl isocyanate, o-tolyl isocyanate, p-tolyl isocyanate, 2-fluorophenyl isocyanate, 3-fluorophenyl isocyanate or 4-fluorophenyl isocyanate;

(4) heterocyclic selected from 5- or 6- membered heterocyclic radicals having 1 to 4 atoms selected from N and O, said heterocyclic radical being unsubstituted or substituted with one or two substituents selected from $C_1$–$C_6$ alkyl, $C_1$–$C_6$ alkoxy, phenyloxy, naphthyloxy, halo, trifluoromethyl, $C_1$–$C_6$ alkanoyloxy, $C_1$–$C_6$ alkanoylamino, carb($C_1$–$C_6$)-alkoxy, $C_1$–$C_6$ alkoxycarbonyl-$C_1$–$C_6$ alkyl or phenyl; e.g. 3-pyridyl isocyanate, 2-pyridyl isocyanate, 4-pyridyl isocyanate, 5-ethyl-2-pyridyl isocyanate, 2-furyl isocyanate, 3-furyl isocyanate, 2-isocyanato tetrahydropyran, 3-isocyanato tetrahydropyran, 4-isocyanato tetrahydropyran or 2-isocyanato pyrimidine.

The following examples are not intended to be limiting but are illustrative of this invention. "Skellysolve B" is a petroleum ether fraction of b.p. 60°–68° C. consisting essentially of n-hexane.

EXAMPLE 1

Formanilide

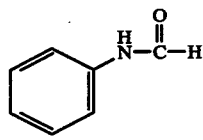

A solution of phenyl isocyanate (1.2 g.; 0.01 mole in 100 ml. anhydrous 1,4-dioxane containing two drops of anhydrous triethylamine was mixed with 500 mg. of 10% Pd-on-carbon and shaken at a pressure of 50 p.s.i. of hydrogen on a Parr low pressure hydrogenator. The uptake of hydrogen was complete in 5 minutes. The catalyst was collected and washed with 50 ml. of 1,4-dioxane. The solvent was evaporated to give 1.2 g. (98% yield) of slightly yellow oil which slowly crystallized. The product was confirmed to be formanilide by ir, nmr and glc analyses.

The above example was repeated except that the triethylamine catalyst was omitted. Under these conditions a yield of 90% was obtained, but the reaction did not reach completion until at least 2.5 hours.

EXAMPLE 2

N-Cyclohexylformamide

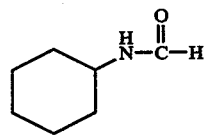

A solution of cyclohexyl isocyanate (1.25 g.; 0.01 mole) in 100 ml. anhydrous 1,4-dioxane containing two drops of anhydrous triethylamine was mixed with 0.5 gram 10% Pd-on-carbon and shaken at a pressure of 50 p.s.i. of hydrogen on a Parr low pressure hydrogenator. The uptake of hydrogen was complete in two hours. Work up, as in Example 1, gave 1.15 g. of colorless oil containing a trace of isocyanate. The product was purified by slurrying the oil with Skellysolve B, chilling at −15° C. and decanting the supernatant from the crystalline formamide. After drying under high vacuum, the weight of title product was 1.06 g. (83.5% yield). The ir, nmr and glc were identical to an authentic sample.

EXAMPLE 3

1-Naphthylformamide

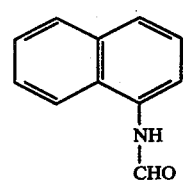

The catalytic hydrogenation procedure of Example 1 was repeated except that the phenyl isocyanate used therein was replaced by 1.7 g. (0.01 mole) of 1-naphthylisocyanate. Reduction was complete in 45 minutes. The catalyst was removed by filtration and the colorless filtrate then evaporated to dryness giving 1.71 g. of tan-white crude product, m.p. 134°–135° C. The solid was recrystallized from ethanol-water to give 1.62 g. (94% yield) of dried title product, m.p. 137.5°–138.5° C.

EXAMPLE 4 n-Butylformamide

CH$_3$(CH$_2$)$_3$NHCHO

The hydrogenation procedure of Example 1 was repeated except that three drops of anhydrous triethylamine was used and the phenyl isocyanate was replaced by 1.98 g. (0.02 mole) of n-butyl isocyanate. Reduction was complete in approximately 45 minutes. The catalyst was removed by filtration and the solvent evaporated under reduced pressure to give 2.1 g. of colorless oil. The oil was vacuum distilled (b.p. 85°–86°/1.8 mm.) to give 1.85 g. (92.5% yield) of title product.

EXAMPLE 5

3-N-Formylaminopyridine

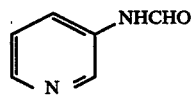

A solution of 1.78 g. (0.0148 mole) of 3-pyridyl isocyanate in approximately 100 ml. of toluene was mixed with 1 g. of 10% Pd-on-carbon catalyst and shaken on a Parr low pressure hydrogenator. (It is noted that since the starting material here is itself a tertiary amine, it is not necessary to employ a separate tertiary amine activation catalyst.) The reduction was allowed to continue for 19 hours. The catalyst was then removed by filtration and washed with methylene chloride. The combined filtrate and wash solution were evaporated to give 463 mg. of an oil. The oil was dissolved in about 10 ml. of acetonitrile, insolubles were filtered off and the filtrate was evaporated to give a solid product. Analysis by infrared and mass spectroscopy confirmed that the major component of the product was 3-N-formylaminopyridine.

EXAMPLE 6

If the general procedures employed in Examples 1–5 are repeated using in place of the isocyanates named therein an equimolar amount of the following isocyanate starting materials:

| R—NCO |
|---|
| R = |
| CH$_3$— |
| C$_2$H$_5$— |
| CH$_3$CH$_2$CH$_2$— |
| (CH$_3$)$_2$CH— |
| CH$_3$(CH$_2$)$_2$CH$_2$— |
| (CH$_3$)$_3$C— |
| CH$_3$(CH$_2$)$_4$CH$_2$— |
| CH$_3$(CH$_2$)$_6$CH$_2$— |
| CH$_3$(CH$_2$)$_{10}$CH$_2$— |
| CH$_3$(CH$_2$)$_{16}$CH$_2$— |

-continued
| R— | NCO |
|---|---|
| R = | |
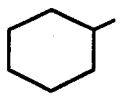
trans-C$_6$H$_5$C$_3$H$_4$-
(trans-2-phenylcyclopropyl)
C$_6$H$_5$
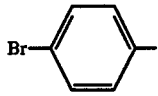
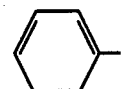
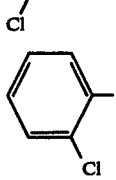
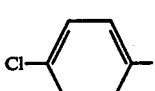
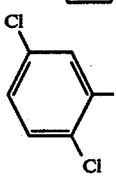
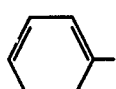
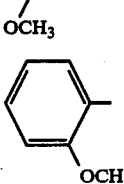
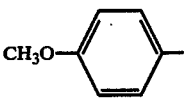
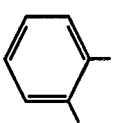
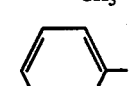
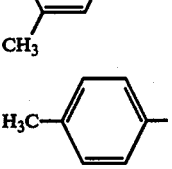
-continued
| R— | NCO |
|---|---|
| R = | |
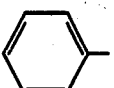
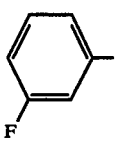
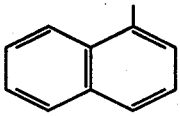
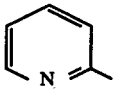
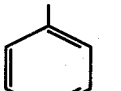
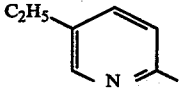
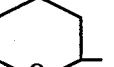
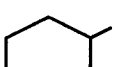
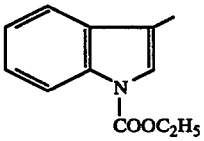

-continued

R—NCO

R =

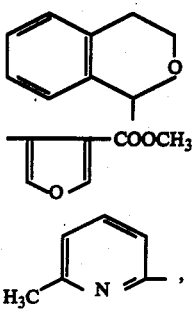

there are produced the corresponding formamide products.

I claim:

1. In the process of reducing an isocyanate functional group —N=C=O to a formamide functional group -NH-CHO, the improvement which comprises hydrogenating a monisocyanate organic compound of the formula R—N=C=O wherein R represents $C_1$-$C_{20}$ alkyl, $C_3$-$C_{12}$ cycloalkyl, aryl selected from phenyl and naphthyl or a heterocyclic group which contains one or more ring hetero atoms selected from oxygen and nitrogen in addition to at least on ring carbon atom and which is linked to the nitrogen atom of the isocyanate moiety through a ring carbon atom, said R group being unsubstituted or substituted by $C_1$-$C_6$ alkyl, $C_1$-$C_6$ alkoxy, phenyloxy, naphthyloxy, halo, trifluoromethyl, $C_1$-$C_6$ alkanoyloxy, $C_1$-$C_6$ alkanoylamino, carb($C_1$-$C_6$)alkoxy, $C_1$-$C_6$ alkoxycarbonyl $C_1$-$C_6$ alkyl or phenyl, with a platinum or pallodium catalyst in an inert aprotic organic solvent in the presence of a catalytic amount of a tertiary amine for a time sufficient to produce the corresponding formamide compound of the formula R—NH—CHO.

2. The process according to claim 1 wherein the noble metal catalyst is 10% palladium-on-carbon, the solvent is dioxane or toluene, the hydrogenation pressure is approximately 50 p.s.i. of hydrogen and the temperature is room temperature.

3. The process according to claim 2 wherein a catalytic amount of triethylamine is employed as an activation catalyst.

* * * * *